US006613055B2

United States Patent
Di Emidio

(10) Patent No.: US 6,613,055 B2
(45) Date of Patent: Sep. 2, 2003

(54) INSTRUMENT FOR THE IMPLANT OF A SURGICAL PLATE FOR OSTEOSYNTHESIS

(75) Inventor: Paolo Di Emidio, Controguerra (IT)

(73) Assignee: Piergiacomi Sud - S.r.l., Monteprandone (IT)

( * ) Notice: Subject to any disclaimer, the term of this patent is extended or adjusted under 35 U.S.C. 154(b) by 176 days.

(21) Appl. No.: 09/963,195

(22) Filed: Sep. 26, 2001

(65) Prior Publication Data

US 2003/0060830 A1 Mar. 27, 2003

(51) Int. Cl.[7] .............................................. A61B 17/88
(52) U.S. Cl. .......................................... 606/99; 606/86
(58) Field of Search ............................. 606/53, 69, 86, 606/91, 99, 100, 206, 105, 62, 63, 67, 68; 81/126, 128, 129, 179

(56) References Cited

U.S. PATENT DOCUMENTS

| | | | | |
|---|---|---|---|---|
| 1,132,146 A | * | 3/1915 | Allen ............................. 81/99 |
| 2,937,551 A | * | 5/1960 | Akers ........................... 81/179 |
| 4,813,407 A | * | 3/1989 | Vogen ........................... 606/86 |
| 5,152,763 A | * | 10/1992 | Johnson ......................... 606/86 |
| 5,176,701 A | * | 1/1993 | Dusek et al. ................. 606/207 |
| 5,366,476 A | * | 11/1994 | Noda ........................... 606/206 |
| 5,505,734 A | * | 4/1996 | Caniggia et al. ............... 606/63 |
| 6,126,674 A | * | 10/2000 | Janzen ......................... 606/206 |

* cited by examiner

Primary Examiner—Kevin Shaver
Assistant Examiner—Michael B. Priddy
(74) Attorney, Agent, or Firm—Armstrong, Westerman and Hattori, LLP

(57) ABSTRACT

The present invention relates to an instrument for the implant of a surgical plate for osteosynthesis, comprising a rod that slides inside a tubular sleeve subject to the action of a return spring, which ends with a circular handle in the rear part and with a point with lateral cut in the front part, whose opening is closed by a small tooth located at the end of the tubular sleeve.

6 Claims, 1 Drawing Sheet

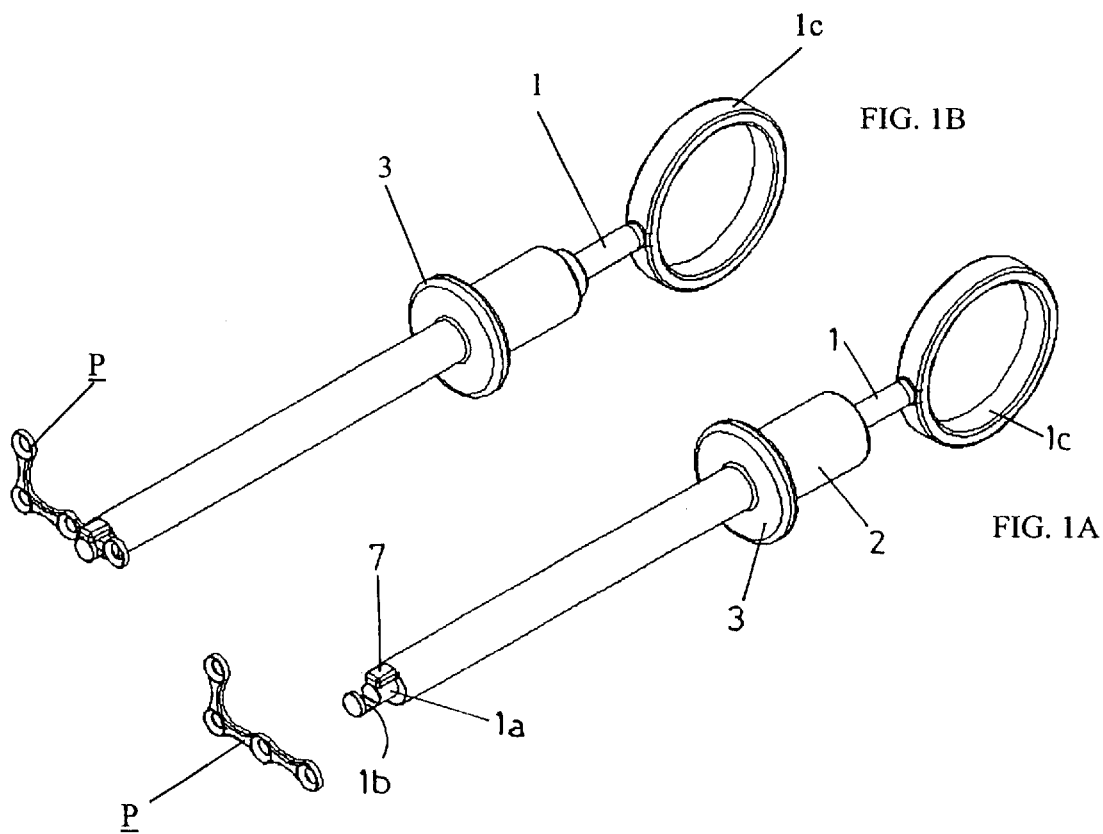
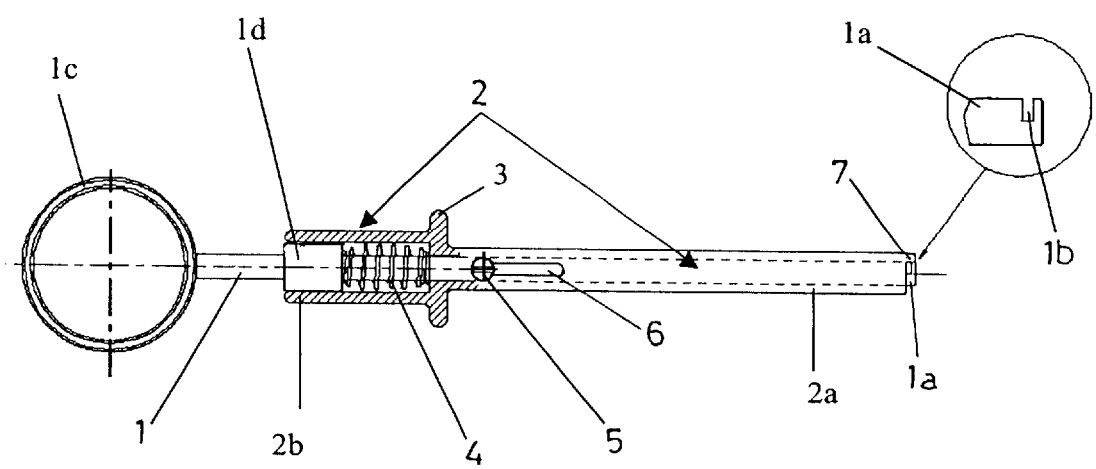

INSTRUMENT FOR THE IMPLANT OF A SURGICAL PLATE FOR OSTEOSYNTHESIS

The present patent application relates to an instrument for the implant of a surgical plate for osteosynthesis.

More precisely, the instrument according to the present invention is used to place and maintain the surgical plate in stable position during the operation, in order to prevent the plate from falling on the soft tissues.

Osteosynthesis systems, that is surgical plates, are frequently used in maxillo-facial traumatology and orthopaedic surgery of maxillary bones, since they guarantee the perfect stability of stumps or fractured bone fragments Today, plates with surgical screws are one of the best containment methods available, capable of ensuring the stability of bone fragments, which is an essential condition for the formation of callus.

In fact, during the preparation of the surgical holes, it is necessary to place the surgical plate in a very accurate way and maintain it stable in the correct position.

No specific surgical instruments are available at the moment for this particular application. For this reason, it is a common practice to use tools that are designed for different purposes and are not very suitable for this application, such as, for example, the surgical-anatomical forceps known as Klemmer forceps, which cannot guarantee satisfactory results in all cases.

On the contrary, the surgical instrument according to the present invention, has the following advantages:

- accurate, stable positioning of the plate during operation;
- good visibility in the operating field;
- ergonomics of the surgical operation.

Substantially, the instrument comprises a rod inserted and sliding inside a cylindrical guide sleeve, from whose front end a small section of the point protrudes, being constantly subject to the action of a return spring that opposes free ejection.

The rear end of the rod protrudes from the other end of the cylindrical sleeve and is provided with a ring in which the operator can insert his thumb to push the rod forward, thus overcoming the resistance of the return spring.

In order to make this operation easier, the sleeve is externally provided with an annular flange, which is hooked between the middle and index fingers until the thumb inserted in the ring is pressed forward.

The point of the rod that protrudes from the sleeve has a calibrated lateral cut, while the front end of the cylindrical sleeve is provided with a small tooth in opposite position with respect to the cut, whose opening is closed by the small tooth.

By pressing and moving the rod forward, the opening of the lateral cut located on the point can be freed by the operator, who can then fix the surgical plate inside the cut, thus engaging it under the small tooth, as soon as the rod is left free to return inside the sleeve because of the action of the return spring.

For major clarity the description of the instrument according to the present invention continues with reference to the enclosed drawings, which are intended for purposes of illustration and not in a limiting sense, whereby, FIGS. 1A and 1B are an axonometric view of the surgical instrument according to the present invention, respectively shown with the point of the rod in ejected and retracted position and the surgical plate engaged in the cut;

FIG. 2 is a lateral view of the surgical instrument according to the present invention, partially sectioned to show the return spring that is housed in the sleeve.

With reference to the above figures, the instrument according to the present invention comprises a rod (1) with a lateral cut (1b) on the point (1a) and a ring (1c) in its rear end.

The rod (1) is inserted and slides inside a cylindrical sleeve (2) composed of two sections (2a, 2b) with different diameter and length, separated by an external annular flange (3).

The front section (2a), with higher length and smaller diameter, exactly houses the rod (1), while the rear section (2b), with smaller length and higher diameter, houses a return spring (4) inserted on the rod (1) and engaged against a collar (1d) located on the rod and housed inside the opening of the rear section (2b).

The travel of the rod (1) inside the sleeve (2) presents two stop points obtained by means of a plug (5) that is radially screwed along the rod (1) and inserted in a longitudinal guide slot (6) located on the body of the sleeve (2) near the annular flange (3).

When the rod (1) is in the rear stop point, the lateral cut (1b) on the point (1a) exactly protrudes on the outside of the front end of the section (2a), which ends with a small tooth (7) that closes the opening of the cut (1b).

When the rod (1) is pressed forward until it reaches the front stop point, the lateral cut (1b) on the point (1a) goes beyond the small tooth (7), so that the opening of the cut (1b) is free to receive the surgical plate (P), as shown in FIG. 2.

What is claimed is:

1. An instrument for implantation of a surgical plate for osteosynthesis comprising:

a rod with a point and a rear end, the rod having a lateral cut on the point and a ring on the rear end;

a cylindrical sleeve composed of a front section and a rear section with different diameter and length, separated by an external annular flange; wherein the front section with higher length and smaller diameter exactly houses the rod and ends with a small tooth;

a return spring housed in the rear section; inserted on the rod and engaged against a collar located on the rod and exactly housed in an opening of the rear section;

a plug radially screwed along the rod and inserted into a longitudinal guide slot located on the sleeve near the annular flange.

2. An instrument for implanting a surgical plate for osteosynthesis, comprising a rod telescopically received within a sleeve for sliding movement therein, stop means for limiting the sliding movement of the rod between a first position in which rod is advanced beyond the sleeve and a second position in which the rod is retracted within the sleeve, resilient means biasing the rod towards its second retracted position within the sleeve, manually-manipulatible means opposing the resilient means for moving the rod forwardly of the sleeve and into the first advanced position, such that a section of the rod extends beyond the sleeve, and the extending section of the rod having a cut-out portion formed therein for receiving the surgical plate to be implanted.

3. The instrument of claim 2, wherein the sleeve has a forwardly-projecting tooth which is circumferentially aligned with the cut-out portion of the rod and covers the cut-out portion when the rod is in its second retracted position relative to the sleeve.

4. The instrument of claim 2, wherein the manually-manipulatible means comprises a ring carried by a portion of the rod extending rearwardly of the sleeve, and an annular flange on the sleeve intermediately of the length thereof, whereby the user may hook the annular flange between his or her middle and index fingers while inserting his or her thumb within the ring for overcoming the bias of the resilient means.

5. The instrument of claim 4, wherein the resilient means comprises a collar on the rod, the collar being slidably received within an enlarged portion of the sleeve disposed rearwardly of the annular flange on the sleeve, and a coil spring piloted on the rod and disposed axially between the collar on the rod and the annular flange on the sleeve.

6. The instrument of claim 2, wherein the stop means comprises a plug carried by the rod and extending radially therefrom, and the sleeve having a longitudinal closed slot for slidably receiving the plug.

* * * * *